US00PP22600P3

(12) United States Plant Patent

Klemm et al.

(10) Patent No.: US PP22,600 P3

(45) Date of Patent: Mar. 20, 2012

(54) *CALIBRACHOA* PLANT NAMED 'KLECA09208'

(50) Latin Name: *Calibrachoa* hybrid
Varietal Denomination: KLECA09208

(75) Inventors: Nils Klemm, Stuttgart (DE); Anita Stoever, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 216 days.

(21) Appl. No.: 12/661,879

(22) Filed: Mar. 25, 2010

(65) Prior Publication Data

US 2011/0239342 P1 Sep. 29, 2011

(51) Int. Cl.
*A01H 5/00* (2006.01)

(52) U.S. Cl. ..... Plt./413

(58) Field of Classification Search ..... Plt./413
See application file for complete search history.

(56) References Cited

OTHER PUBLICATIONS

UPOV ROM GTITM Computer Database, GTI Jouve Retrieval Software 2011/05 CA Citation for 'KLECA09208'.*
UPOV ROM GTITM Computer Database, GTI Jouve Retrieval Software 2011/05 QZ Citation for 'KLECA09208'.*
Anonymous 2012 Selecta Catalog. pp. 18-25 Date Unknown.*

* cited by examiner

*Primary Examiner* — Wendy C Haas
(74) *Attorney, Agent, or Firm* — Jondle & Associates, P.C.

(57) ABSTRACT

A new *Calibrachoa* plant named 'KLECA09208' particularly distinguished by double flowers which are stable in heat, a very early flowering period with a short cultivation time of seven to eight weeks for a finished flowering plant, very good heat and rain tolerance, and excellent performance in landscape, is disclosed.

1 Drawing Sheet

Genus and species: *Calibrachoa* hybrid.
Variety denomination: 'KLECA09208'.

BACKGROUND OF THE NEW PLANT

The present invention comprises a new and distinct variety of *Calibrachoa,* botanically known as *Calibrachoa* hybrid and hereinafter referred to by the variety name 'KLECA09208'. The new variety was discovered as a seedling resulting from a cross conducted in June 2006 in Stuttgart, Germany. The female parent was the proprietary *Calibrachoa* plant 'CA060322' (unpatented), while the male parent was the proprietary *Calibrachoa* plant 'W220' (unpatented).

The new variety was first propagated via vegetative cuttings in May 2007 in Stuttgart, Germany and has been asexually reproduced by vegetative cuttings and in-vitro propagation in Stuttgart, Germany for more than 50 generations. The present invention has been found to retain its distinctive characteristics through successive asexual propagations.

Plant Breeder's Rights for this variety have been applied for in Canada on Mar. 25, 2009. 'KLECA09208' has not been made publicly available or sold more than one year prior to the filing date of this application.

SUMMARY OF THE INVENTION

The following are the most outstanding and distinguishing characteristics of this new variety when grown under normal horticultural practices in Stuttgart, Germany.

1. Double flowers that are stable in heat;
2. Very early flowering period with a short cultivation time of seven to eight weeks for a finished flowering plant;

3. Very good heat and rain tolerance, excellent performance in landscape.

DESCRIPTION OF THE PHOTOGRAPH

This new *Calibrachoa* plant is illustrated by the accompanying photograph which shows flowers and foliage of the plant. The colors shown are as true as can be reasonably obtained by conventional photographic procedures. The photograph was taken in May 2009 of a 5-month-old *Calibrachoa* plant, grown in a greenhouse in Stuttgart, Germany.

DESCRIPTION OF THE NEW VARIETY

The following detailed descriptions set forth the distinctive characteristics of 'KLECA09208'. The data which defines these characteristics were collected from asexual reproductions carried out in Stuttgart, Germany. The plant history was taken in May 2009 on 5-month-old plants which were planted as rooted cuttings in an 11 centimeter pot and then grown in a glass greenhouse. The plants had one terminal pinch one week after potting. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:

*Family.*—Solanaceae.
*Botanical.*—*Calibrachoa* sp.
*Denomination.*—'KLECA09208'.
*Common.*—*Calibrachoa Hybrida.*

Parentage:

*Female.*—The proprietary *Calibrachoa* plant 'CA060322' (unpatented).

*Male.*—The proprietary *Calibrachoa* plant 'W220' (unpatented).

Growth:

*Form.*—Compact.

*Habit.*—Flat trailing.

*Height* (*measured from the top of the soil*).—4.0 cm to 6.0 cm.

*Width* (*horizontal plant diameter*).—15.0 cm.

*Time to produce a finished flowering plant.*—7 to 8 weeks.

*Outdoor plant performance.*—Continuously flowering, stable double flowers, very healthy, good rain tolerance, very good for landscape, heat tolerant.

*Time to initiate and develop roots.*—18 days.

*Root description.*—Fine, fibrous, freely branching, moderate density, white roots.

Stems:

*Length of basal branches.*—8.0 cm.

*Internode length.*—1.5 cm.

*Diameter of branches* (*from midpoint*).—6.0 cm to 8.0 cm.

*Color.*—RHS 144B.

*Texture.*—Smooth.

*Anthocyanin.*—Absent.

*Pedicel.*—Color: RHS 144C. Length: 1.3 cm. Diameter: 0.1 cm. Texture: Smooth.

Leaves:

*Arrangement.*—Alternate, simple, sessile.

*Size.*—Length: about 2.5 cm to 3.5 cm. Width: 0.8 cm to 1.0 cm.

*Shape.*—Lanceolate to elliptic.

*Apex.*—Obtuse to slightly acute.

*Base.*—Attenuate.

*Margin.*—Entire.

*Color.*—Immature leaves: Upper surface: RHS 146B. Lower surface: RHS 146C. Mature leaves: Upper surface: RHS 146A. Lower surface: RHS 147C.

*Texture* (*both upper and lower surfaces*).—Smooth.

*Venation pattern.*—Pinnate.

*Petioles.*—Absent.

Flower bud:

*Shape.*—Irregular to oblong.

*Size.*—Length: 2.2 cm. Diameter: 0.5 cm.

*Color at tight bud.*—RHS 84C.

Inflorescence:

*Blooming habit.*—Flowers face upright, double flowering, axillary.

*Inflorescence type.*—Determinate inflorescence.

*Floret type.*—Double flower.

*Lastingness of individual blooms on the plant.*—6 days.

*Fragrance.*—Absent.

Flowers:

*Immature flower.*—Diameter: Horizontal: 2.8 cm. Vertical: 2.2 cm. Color: Upper surface: RHS 84A. Lower surface: RHS 84B.

*Mature flower.*—Diameter: Horizontal: 3.0 cm. Vertical: 2.5 cm. Color: Upper surface: RHS 84B. Lower surface: RHS 84C.

*Corolla tube.*—Color inside: RHS 5A. Color outside: RHS 1D. Tube length: 1.5 cm. Texture (both inside and outside): Smooth.

*Petals.*—Apex: Obverse. Base: Open, fused into the tube. Margin: Entire. Waviness of petals: Very weak. Lobation: Very weak. Texture (both upper and lower surfaces): Smooth.

*Sepals.*—Calyx (composition): Actinomorphic. Shape: Lanceolate to elliptic. Apex: Acute. Base: Open, tube fused into the base. Margin: Entire. Length: 1.5 cm. Width: 0.3 cm. Color: Upper surface: RHS 146A. Lower surface: RHS 146B. Texture (both upper and lower surfaces): Smooth.

Reproductive organs:

*Stamens.*—Absent.

*Pollen quantity.*—None.

*Pistils.*—Number: 1. Length: 1.1 cm. Diameter: 0.1 cm. Stigma color: RHS 145A.

*Style color.*—RHS 145A.

Fruit and seed set: No fruit or seed set observed.

Disease and insect resistance: No particular resistance or susceptibility has been observed.

COMPARISON WITH PARENTAL AND COMMERCIAL VARIETIES

'KLECA09208' differs from the female parent *Calibrachoa* plant 'CA060322' (unpatented) in that 'KLECA09208' has double violet flowers, while 'CA060322' has semi-double lavender flowers. 'KLECA09208' differs from the male parent *Calibrachoa* plant 'W220' (unpatented) in that 'KLECA09208' has double violet flowers, while 'W220' has single, light blue flowers. 'KLECA09208' differs from the commercial variety 'KLECA08170' (U.S. Plant Pat. No. 21,061) in that 'KLECA09208' has a very early flowering period and double flowers, while 'KLECA08170' has an early flowering period and single flowers.

We claim:

1. A new and distinct variety of *Calibrachoa* plant named 'KLECA09208' as shown and described herein.

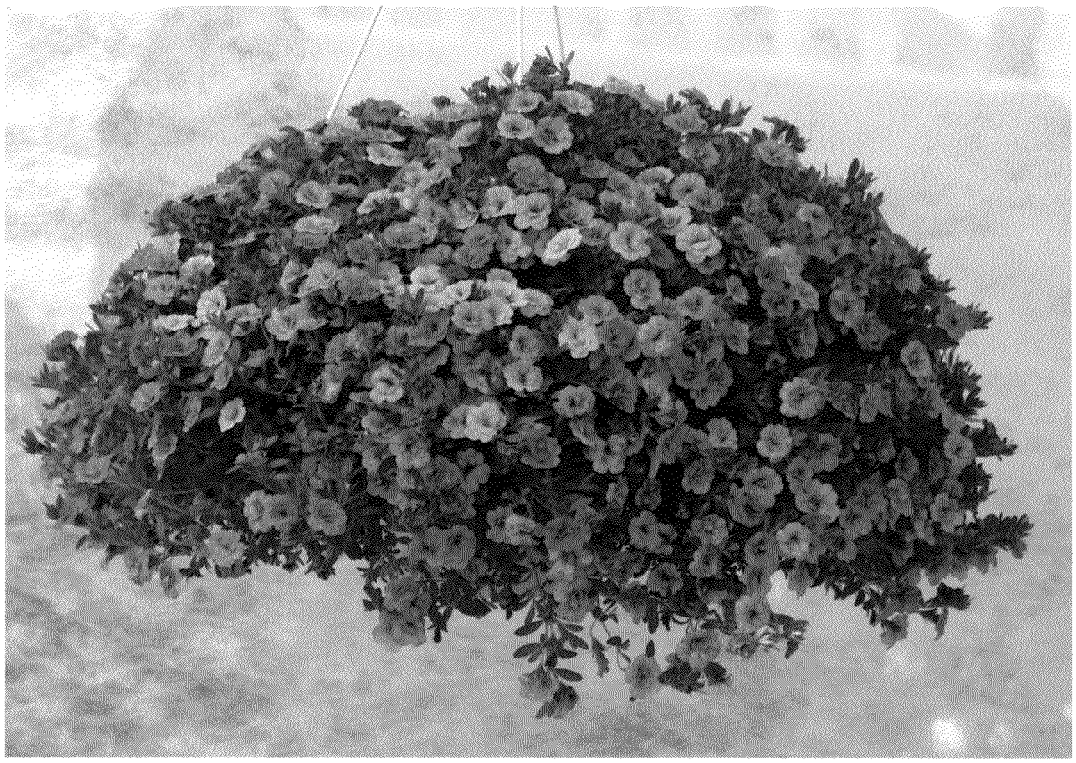

* * * * *